(12) United States Patent
Huang et al.

(10) Patent No.: US 11,154,482 B2
(45) Date of Patent: *Oct. 26, 2021

(54) PEPTIDE, COMPOSITION AND METHOD FOR ANTI-HAIR GRAYING

(71) Applicant: Renorigin Innovation Institute Co., Ltd., Taipei (TW)

(72) Inventors: Hsiu-Chin Huang, Taipei (TW); Hsuan Lin, Taipei (TW)

(73) Assignee: RENORIGIN INNOVATION INSTITUTE CO., LTD., Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 17/036,529

(22) Filed: Sep. 29, 2020

(65) Prior Publication Data
US 2021/0212917 A1 Jul. 15, 2021

Related U.S. Application Data

(62) Division of application No. 16/742,195, filed on Jan. 14, 2020, now abandoned.

(51) Int. Cl.
*A61K 8/64* (2006.01)
*A61Q 5/00* (2006.01)
*A61Q 5/12* (2006.01)

(52) U.S. Cl.
CPC .............. *A61K 8/64* (2013.01); *A61Q 5/004* (2013.01); *A61Q 5/12* (2013.01); *A61K 2800/40* (2013.01)

(58) Field of Classification Search
None
See application file for complete search history.

(56) References Cited

U.S. PATENT DOCUMENTS

2017/0239161 A1* 8/2017 Huang .................... A61Q 5/06
2017/0296629 A1 10/2017 Hirahashi et al.

FOREIGN PATENT DOCUMENTS

CN 103382217 A 11/2013

OTHER PUBLICATIONS

Huertas, Nataly de Jesus et al., "Antimicrobial activity of trunctaed and polyvalent peptides derived from the fkcrrwqwrmkkgla sequence against *Escherichia coli* atc 25922 and *Staphylococcus aureus* atc 25923." Molecules (2017) 22(987).*
Kerwin, Bruce A., "Polysorbates 20 and 80 Used in the Formulation of Protein Biotherapeutics: Structure and Degradation Pathways". Journal of Pharmaceutical Sciences, vol. 97, No. 8, Aug. 2008, pp. 2924-2935.

* cited by examiner

*Primary Examiner* — Fred H Reynolds
(74) *Attorney, Agent, or Firm* — Birch, Stewart, Kolasch & Birch, LLP

(57) ABSTRACT

An isolated peptide consisting of FKCRRWQWRMKKL (SEQ ID NO: 1) for preserving the natural color of the hair, or slowing the decay in the natural pigment production of the hair follicle, or reducing the appearance of hair graying is provided. Also disclosed herein are methods and compositions for preserving the natural color of the hair, or slowing the decay in the natural pigment production of the hair follicle, or reducing the appearance of hair graying in a mammal subject.

4 Claims, 4 Drawing Sheets
(1 of 4 Drawing Sheet(s) Filed in Color)
Specification includes a Sequence Listing.

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Peptide

<400> SEQUENCE: 1

Phe Lys Cys Arg Arg Trp Gln Trp Arg Met Lys Lys Leu
1               5                   10
```

PEPTIDE, COMPOSITION AND METHOD FOR ANTI-HAIR GRAYING

FIELD OF THE INVENTION

This application is a Divisional of co-pending U.S. application Ser. No. 16/742,195 filed on Jan. 14, 2020. The entire content of this application is hereby incorporated by reference.

The present invention pertains to a peptide for preserving the natural color of the hair, or slowing the decay in the natural pigment production of the hair follicle, or reducing the appearance of hair graying in mammals, and methods and compositions thereof.

BACKGROUND OF THE INVENTION

Human scalp hair contains melanin, which is produced in melanocytes in hair follicles and provides effects for the protection of the head from harmful ultraviolet (UV) light, the elimination of toxic heavy metals and chemicals, and the attractive appearance.

Hair gets its natural color based on the quantity, the quality, and the distribution of the melanin, which contains black to brown eumelanin and yellow to reddish-brown pheomelanin.

Hair graying (canities), the loss of pigment production and deposition within the hair shafts, is a noticeable and undesired sign in many cultures. In addition to the aging process, the causes of gray hair have been linked to genetic defects, hormones, pollutants, toxins, and chemical exposure.

Moreover, it's also been known that hair turns gray due to a natural buildup of hydrogen peroxide in hair follicles, giving rise to oxidative stress and graying.

It is still desired to have an effective treatment that could prevent, slow, reduce or reverse hair graying.

BRIEF SUMMARY OF THE INVENTION

It is unexpectedly found in the present invention that a peptide has anti-oxidative activity and effectively prevents and protects cells from oxidative stress, wherein the peptide consists of an amino acid sequence FKCRRWQWRMKKL (SEQ ID NO: 1).

It is found that the peptide of the present invention is able to prevent the bleaching of hair induced by hydrogen peroxide.

Accordingly, in one aspect, the present invention relates to an isolated peptide with an amino acid sequence FKCRRWQWRMKKL (SEQ ID NO: 1) for preserving the natural color of the hair, or slowing the decay in the natural pigment production of the hair follicle, or reducing the appearance of hair graying.

In another aspect, the present invention provides an isolated peptide for preserving the natural color of the hair, or slowing the decay in the natural pigment production of the hair follicle, or reducing the appearance of hair graying in a mammal subject. The isolated peptide consists of an amino acid sequence FKCRRWQWRMKKL (SEQ ID NO: 1).

In further aspect, the present invention provides a composition for preserving the natural color of the hair, or slowing the decay in the natural pigment production of the hair follicle, or reducing the appearance of hair graying in a mammal subject. The composition comprises an effective amount of an isolated peptide consisting of an amino acid sequence as set forth in SEQ ID NO: 1. According to certain embodiments of the invention, the composition may further comprise an acceptable carrier, and may be formulated as a topical formulation.

According to the present invention, the topical formulation may comprise an ointment, an aerosol, a lotion, a cream, a gel, drops, a spray, a liquid, a patch, a shampoo or a hair conditioner. In one preferred embodiment, the composition is formulated as a shampoo or a hair conditioner.

In yet further aspect, the present invention features a method for preserving the natural color of the hair, or slowing the decay in the natural pigment production of the hair follicle, or reducing the appearance of hair graying in a subject in need thereof, which comprises administering to the subject the composition of the present invention in an amount effective to prevent and/or protect hairs from bleaching in the subject. In preferred embodiments of the invention, the method is used to preserve the natural color of the hair, or slow the decay in the natural pigment production of the hair follicle, or reduce the appearance of hair graying of the mammal subject, preferably a human subject. In preferred embodiments of the invention, the composition is administered topically to the subject.

It is to be understood that both the foregoing general description and the following detailed description are exemplary and explanatory only and are not restrictive of the invention.

BRIEF DESCRIPTION OF THE SEVERAL VIEWS OF THE DRAWINGS

The patent or application file contains at least one color drawing. Copies of this patent or patent application publication with color drawing will be provided by the USPTO upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred.

In the drawings:

FIG. 1 shows a result of DPPH assay. 50 µg/ml peptide of SEQ ID NO: 1 was treated with 0.2 mM DPPH for 16 h. Data are represented as the means±SD from three independent experiments. ***$p<0.001$.

FIG. 2 shows a preventive effect of the peptide of the invention against hydrogen peroxide-induced oxidative stress injury. Data are represented as the means±SD from three independent experiments. ***$p<0.001$.

FIG. 3 shows a protection effect of the peptide of the invention against hydrogen peroxide-induced oxidative stress injury. Data are represented as the means±SD from three independent experiments. ***$p<0.001$.

Figure 4:
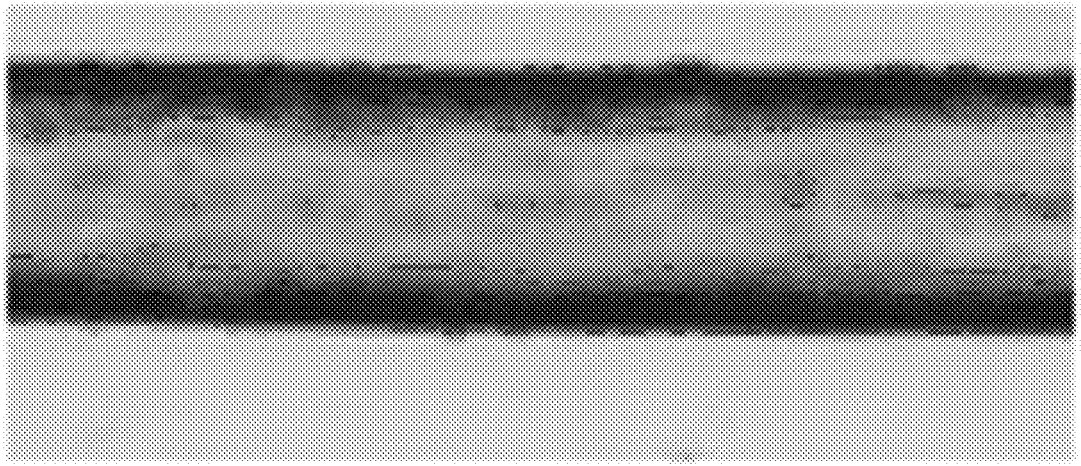
Figure 4:
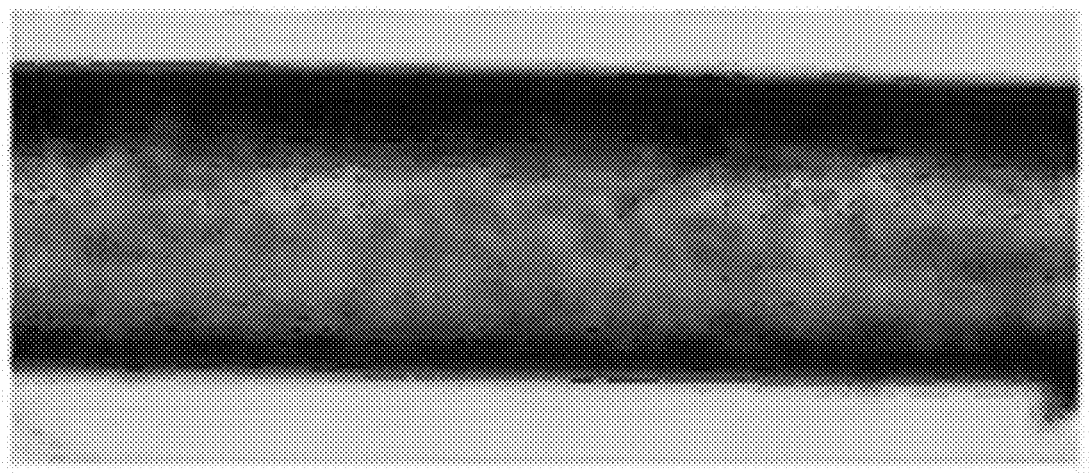

FIG. 4 provides photographs of the hairs decolored with 7.5% hydrogen peroxide. Top panel, 7.5% hydrogen peroxide only; bottom panel, 7.5% hydrogen peroxide and incubated with 400 µg/ml peptide of the invention.

DETAILED DESCRIPTION OF THE INVENTION

Unless otherwise defined herein, scientific and technical terms used herein have the meanings that are commonly understood by those of ordinary skill in the art.

As used herein, the singular forms "a", "an", and "the" include plural referents unless the context clearly dictates otherwise. Thus, for example, reference to "a sample"

includes a plurality of such samples and equivalents thereof known to those skilled in the art.

The term "gray hair" or "hair graying" as used herein refers to the hair that has changed its color from the original natural hair color due to biological processes such as aging, chemical exposure, environmental exposure, nutritional exposure, medicine exposure and the like, and is of reduced color, or achromatic color, or an intermediate between white and black that is lighter than the original natural hair color.

The term "peptide" is used herein in its conventional sense, i.e., a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. Standard abbreviations for amino acids are used.

The term "peptide for preserving the natural color of the hair, or slowing the decay in the natural pigment production of the hair follicle, or reducing the appearance of hair graying" as used herein refers to a peptide that has substantial preventive and/or protective activities against hair bleaching. Preferably, peptides up to about 100 amino acid residues or 90, or 80, or 70, or 60, or 50, or 40, or 30, or 25, or 20, or 15, or 13 amino acids are included for having said activities.

The term "subject" as used herein can be any animal classified as a mammal, including a human.

The term "carrier" as used herein refers to materials commonly used on the formulation of pharmaceutical or cosmetic composition used to enhance stability, sterility and deliverability. When the peptide delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. The compositions may contain physiologically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The term "topical" or "topically" as used herein its conventional sense as referring to a spot which can be in or on any part of the body, including but not limited to the epidermis, any other dermis, or any other body tissue. Topical administration or application means the direct contact of the peptide with tissue, such as skin or membrane which contains melanin-producing cells.

In some embodiments, the present invention provides an isolated peptide effectively for preserving the natural color of the hair, or slowing the decay in the natural pigment production of the hair follicle, or reducing the appearance of hair graying, wherein the peptide consists of an amino acid sequence FKCRRWQWRMKKL (SEQ ID NO: 1).

In some embodiments, the present invention provides a composition for preserving the natural color of the hair, or slowing the decay in the natural pigment production of the hair follicle, or reducing the appearance of hair graying in a mammal subject. The composition comprises an effective amount of an isolated peptide consisting of an amino acid sequence as set forth in SEQ ID NO: 1. According to certain embodiments of the invention, the composition may further comprise an acceptable carrier, and may be formulated as a topical formulation.

In some embodiments, the topical formulation may comprise an ointment, an aerosol, a lotion, a cream, a gel, drops, a spray, a liquid, a patch, a shampoo or a hair conditioner. In one preferred embodiment, the composition is formulated as a shampoo or a hair conditioner.

In some embodiments, the present invention provides a method for preserving the natural color of the hair, or slowing the decay in the natural pigment production of the hair follicle, or reducing the appearance of hair graying in a subject in need thereof, which comprises administering to the subject the composition of the present invention in an amount effective to prevent and/or protect hairs from bleaching in the subject. In preferred embodiments of the invention, the method is used to inhibit hair graying of the mammal subject, such as a human subject. In preferred embodiments of the invention, the composition is administered topically to the subject.

The present invention provides the use of the isolated peptide consisting of an amino acid sequence as set forth in SEQ ID NO: 1 as an active ingredient for various uses. In one preferred embodiment, the isolated peptide of the present invention is combined with an acceptable carrier to form a topical formulation which may be placed on the skin. Topical formulations may comprise an ointment, lotion, paste, cream, gel, drop, suppository, spray, liquid, shampoo, hair conditioner, powder and transdermal patch. Thickeners, diluents, emulsifiers, dispersing aids or binders may be used as needed. Preferably, one function of the carrier is to enhance skin penetration of the peptide of the present invention, and should be capable of delivering the peptide to melanocytes under in vivo conditions. Suitable carriers are well known to one of ordinary skill, and include but are not limited to water, dimethylsulfoxide, ethanol, liposome, liquid petrolatum, petrolatum dimethylformamide, 2-pyrrolidone, oleic acid, and Azone® brand penetration enhancer.

The composition according to the present invention may contain, in addition to the above-mentioned substances, other ingredients which can give a beneficial effect to the main effect, to the extent that the main effect is not impaired. The composition may further comprise a humectant, an emollient, an ultraviolet absorber, an antiseptic, a bactericide, a pH adjuster, an organic or inorganic pigment, a perfume, a cold agent or a limiting agent. The compounding amount of the above components can be easily selected by a person skilled in the art within the range not impairing the object and effect of the present invention.

The composition disclosed in the present invention may further include, for example, an antioxidant. Examples of other antioxidants include hematin, vitamin C, and vitamin E.

The present invention is further illustrated by the following examples, which are provided for the purpose of demonstration rather than limitation.

EXAMPLES

1. Sample Preparation

Peptide of SEQ ID NO: 1 were synthesized by Genomics Bioscience & Technology co. Ltd (Taipei, Taiwan) and the purity and composition of these peptides was confirmed by high performance liquid chromatography (HPLC) and mass spectrometry. Peptide stocks were prepared by dissolving 10 mg of lyophilized peptide powder in 1 ml of double deionized water (ddH2O), and then stored at −20° C.

2. DPPH Assay

50 μg/ml peptide of SEQ ID NO: 1 was added in 96-well plates and incubated with 0.2 mM DPPH. Plates incubated in the dark for 16 hours at room temperature. After 16 h, the absorbance was measured at 515 nm using an automated plat reader (molecular devices).

3. Cell Culture

B16F10 murine melanoma cells (American Type Culture Collection, Manassas, Va., USA) were cultured in Dulbecco's modified Eagle's medium (DMEM) (Thermo Scientific, Barrington, Ill., USA) with 10% fetal bovine serum (FBS) (Gibco, Grand Island, N.Y., USA) and penicillin/streptomycin (100 IU/50 g/ml) in a humidified atmosphere containing 5% $CO_2$ at 37° C.

4. Cell Viability Assay

Cells ($1 \times 10^3$) were seeded in 96-well plates. After treatment with hydrogen peroxide and peptide of SEQ ID NO: 1, MTT was added to a final concentration of 0.5 mg/ml and incubated for 4 h at 37° C. to allow MTT reduction. The formazan crystals were then dissolved in 10% sodium dodecyl sulfate (SDS) containing 0.01 N HCl and absorbance was measured at the dual wavelengths of 570 and 630 nm with a spectrophotometer (VersaMax; Molecular Devices, Silicon Valley, Calif., USA).

5. Bleaching of Hair

Hairs were treated with 7.5% hydrogen peroxide with or without peptide of SEQ ID NO: 1 for 14 days.

Results

1. DPPH Assay

Figure 1:
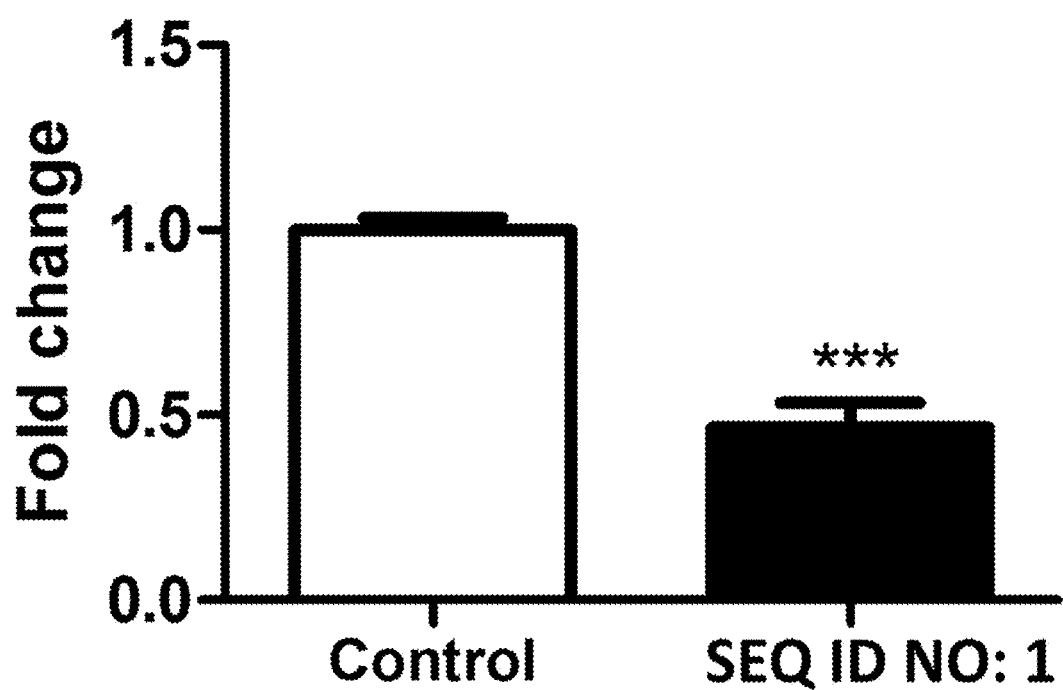

Peptide of SEQ ID NO: 1 significantly decreased DPPH radical scavenging capacity (FIG. 1).

2. Prevention of Hydrogen Peroxide-Induced Oxidative Stress Injury

Figure 2:
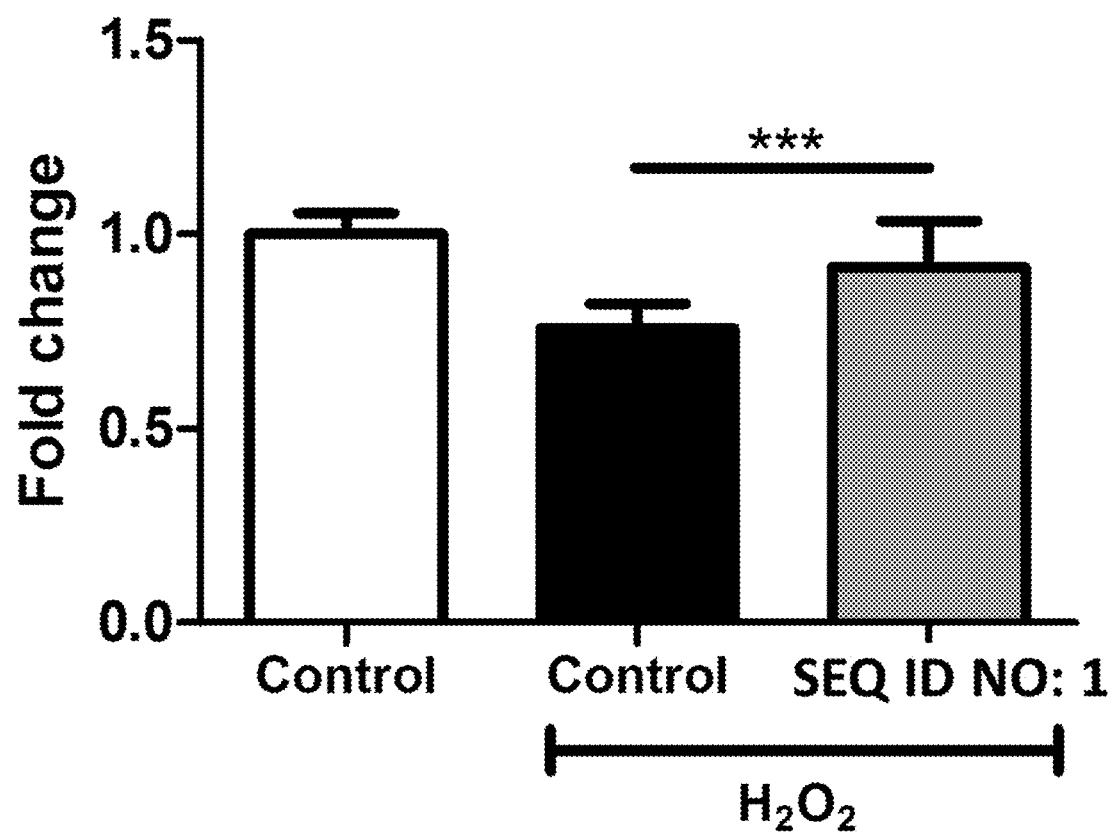

Cells were treated with 50 μg/ml peptide of SEQ ID NO: 1 for 24 h and then exposed to 0.5 mM hydrogen peroxide for 2 h. MTT assay showed that peptide of SEQ ID NO: 1 attenuates hydrogen peroxide-induced stress injury (FIG. 2).

3. Protection Against Hydrogen Peroxide-Induced Oxidative Stress Injury

Figure 3:
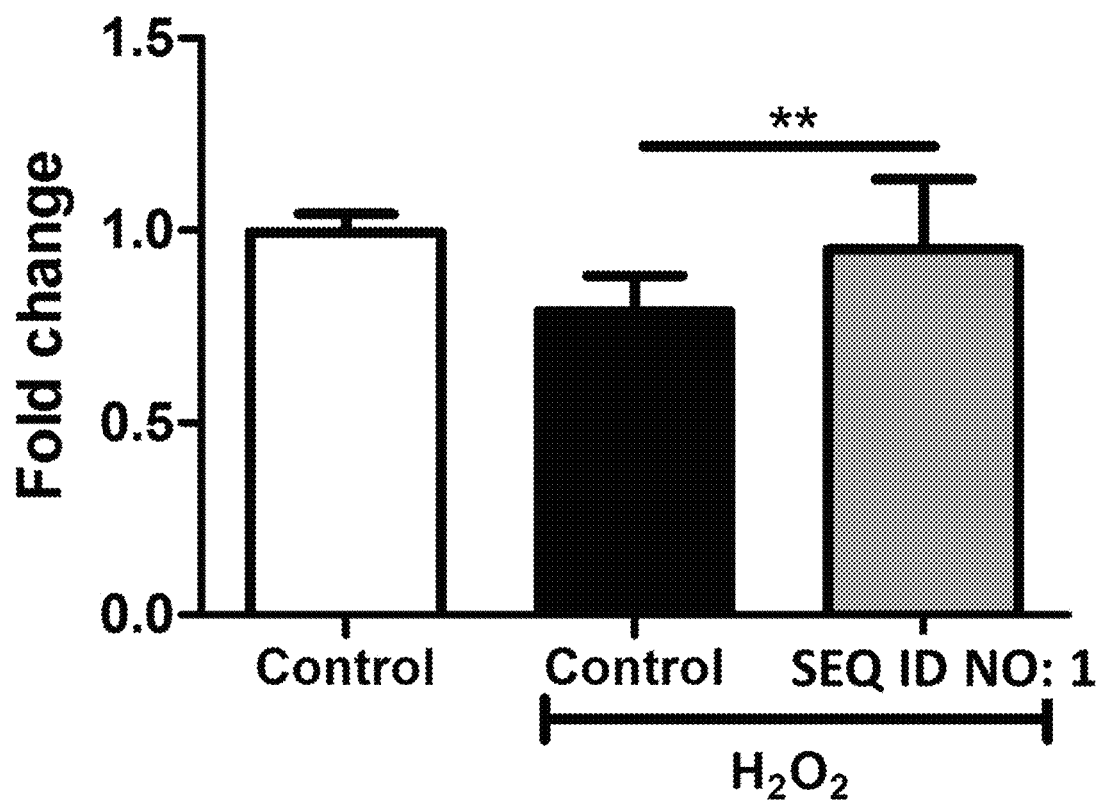

Cells were exposed to 30 μM hydrogen peroxide for 24 h and then treated with 50 μg/ml peptide of SEQ ID NO: 1 and hydrogen peroxide for 48 h. MTT assay showed that peptide of SEQ ID NO: 1 attenuates hydrogen peroxide-induced stress injury (FIG. 3).

4. Bleaching of Hair

Hair showed significant color change (white) after hydrogen peroxide immersion. However, hair still had bright yellow after treated with hydrogen peroxide in the presence of peptide of SEQ ID NO: 1 (FIG. 4).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

---

---

What is claimed is:

1. A method for preserving the natural color of the hair, or slowing the decay in the natural pigment production of the hair follicle, or reducing the appearance of hair graying in a subject in need thereof, comprising
   administering to the subject a composition comprising an isolated peptide consisting of an amino acid sequence of SEQ ID NO: 1 at an amount effective to inhibit hair graying in the subject.

2. The method of claim 1, wherein the composition is administered to the subject topically.

3. The method of claim 1, wherein the composition is in the form of a shampoo.

4. The method of claim 1, wherein the composition is in the form of a hair conditioner.

* * * * *